US009645129B2

(12) United States Patent
Romanak et al.

(10) Patent No.: US 9,645,129 B2
(45) Date of Patent: *May 9, 2017

(54) PROCESS-BASED APPROACH FOR THE DETECTION OF DEEP GAS INVADING THE SURFACE

(71) Applicant: Board of Regents, The University of Texas System, Austin, TX (US)

(72) Inventors: Katherine Romanak, Austin, TX (US); Philip C. Bennett, Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 115 days.

This patent is subject to a terminal disclaimer.

(21) Appl. No.: 14/318,087

(22) Filed: Jun. 27, 2014

(65) Prior Publication Data
US 2015/0004708 A1   Jan. 1, 2015

Related U.S. Application Data

(60) Provisional application No. 61/840,224, filed on Jun. 27, 2013.

(51) Int. Cl.
G01N 33/24   (2006.01)
(52) U.S. Cl.
CPC .................... *G01N 33/24* (2013.01)
(58) Field of Classification Search
CPC ....... G01N 33/241; G01N 33/24; G01N 33/00
USPC ................................................... 436/29, 25
See application file for complete search history.

(56) References Cited

U.S. PATENT DOCUMENTS

| | | | |
|---|---|---|---|
| 7,704,746 | B1 | 4/2010 | White |
| 8,681,336 | B2 | 3/2014 | Nickerson et al. |
| 8,714,034 | B2 | 5/2014 | Zimbron et al. |
| 8,772,720 | B2 | 7/2014 | Chae et al. |
| 2010/0241363 | A1 | 9/2010 | Keeling et al. |
| 2011/0068940 | A1 | 3/2011 | Kim et al. |

FOREIGN PATENT DOCUMENTS

WO      2014210509 A1   12/2014

OTHER PUBLICATIONS

Romanak, K. D., et al, Process-based approach to CO2 leakage detection by vadose zone gas monitoring at geologic CO2 storage sites, Geophysical Research Letters, vol. 39, L15405, Aug. 15, 2012, pp. 1-6.*
Auxiliary Material for Process-based approach to CO2 leakage detection by vadose zone gas monitoring at geologic CO2 storage sites, Jul. 31, 2012, pp. 1-21.*
International Preliminary Report on Patentability, PCT/US2014/044657, PCT, ISR generated on Dec. 29, 2015, pp. 1-7.*
The IEA Weyburn CO2 Monitoring and Storage Project, Final report of the European research team, British Geological Survey, Natural Environmental Research Council, 2005 pp. 1-54, in particular pp. 32-38 and 45-47.*
Romanak, Katherine, Vadose-Zone Geochemistry of Playa Wetlands, High Plains, Texas, The University of Texas at Austin, Dec. 1997, pp. 1-293.*
European Commission, Directive 2009/31/EC of the European Parliament and of the Council of Apr. 23, 2009 on the geological storage of carbon dioxide and amending Council Directive 85/337/EEC, European Parliament and Council Directives 2000/60/EC, 2001/80/EC, 2004/35/EC, 2006/12/EC, 2008/1/EC and Regulation (EC) No. 1013/2006 Text with EEA relevance: Official Journal of the European Union L 140, May 6, 2009, p. 0114-0135.
Fryar, et al., "Nitrate reduction during ground-water recharge, Southern High Plains, Texas", Journal of Contaminant Hydrology 40, (2000), 335-363.
Furche, et al. "One year continuous vadose zone gas monitoring above an EGR test site" Geophysical Research Abstracts vol. 12, EGU2010-3095-1, 2010 7th EGU General Assembly 2010.
Gustavson, et al. "Depositional facies of the Miocene-Pliocene Ogallala Formation, northwestern Texas and eastern New Mexico" Geology, Mar. 1988, 16(3): 203-206.
Hanson, et al. "Separating root and soil microbial contributions to soil respiration: A review of methods and observations" Biogeochemistry, 48: 115-146, 2000.
Hovorka, S.D., "Quaternary evolution of playa lakes on the Southern High Plains—a case study from the Amarillo area, Texas" The University of Texas at Austin, Bureau of Economic Geology Report of Investigations No. 236, 52 p. 1995.
Martin, et al. "Simultaneous Determination of Argon and Nitrogen" Ground Water 33(5): 781-785, Sep. 1995.
Riding, et al., "Subsurface characterisation and geological monitoring of the CO2 injection operation at Weyburn, Saskatchewan, Canada" D.J. Evans and R.A. Chadwick, eds., Underground gas storage: worldwide experiences and future development in the UK and Europe: London, Geological Society, Special Publication 313: 227-256, 2009.
Romanak, K.D. "Vadose-Zone Geochemistry of Playa Wetlands, High Plains, Texas" The University of Texas at Austin, Ph.D. dissertation, 1997, 273 p.
USEPA "General Technical Support Document for Injection and Geologic Sequestration of Carbon Dioxide: Subparts RR and UU" Office of Air and Radiation U.S. Environmental Protection Agency, Nov. 2010, 98 pp.
USEPA "Mandatory Reporting of Greenhouse Gases: Injection and Geologic Sequestration of Carbon Dioxide; Final Rule" Federal Register, vol. 75, No. 230, Dec. 1, 2010, 31 pp.

(Continued)

*Primary Examiner* — Christine T Mui
(74) *Attorney, Agent, or Firm* — Kilpatrick Townsend & Stockton LLP (57)   ABSTRACT

The present invention includes a method for determining the level of deep gas in a near surface formation that includes: measuring $CO_2$, $O_2$, $CH_4$, and $N_2$ levels in percent by volume from one or more surface or near surface geological samples; adding the water vapor content to the measured $CO_2$, $O_2$, $CH_4$, and $N_2$ levels in percent by volume; normalizing the gas mixture to 100% by volume or 1 atmospheric total pressure; and determining the ratios of: $O_2$ versus $CO_2$ to distinguish in-situ vadose zone $CO_2$ from exogenous deep leakage $CO_2$; $CO_2$ versus $N_2$ to distinguish whether $CO_2$ is being removed from the near surface formation or $CO_2$ is added from an exogenous deep leakage input; or $CO_2$ versus $N_2/O_2$ to determine the degree of oxygen influx, consumption, or both; wherein the ratios are indicative of natural in situ $CO_2$ or $CO_2$ from the exogenous deep leakage input.

20 Claims, 6 Drawing Sheets

(56) References Cited

OTHER PUBLICATIONS

Whalen, et al. "Rapid Methane Oxidation in a Landfill Cover Soil" Applied Environmental Microbiology, Nov. 1990, 56(11): 3405-3411.

Whiticar, Michael J. "Carbon and Hydrogen Isotope Systematics of Bacterial Formation and Oxidation of Methane" Chemical Geology, 161: 291-314, 1999.

Non-Final Office Action Mailed May 4, 2016, for U.S. Appl. No. 14/317,836, 28 pages.

Whittaker, Steve, "IEA GHG Weyburn-Midale CO2 Storage and Monitoring Project, in Regional Carbon Sequestration Partnerships Annual Review" Oct. 5, 2010.

Whittaker, et al., "IEA GHG Weyburn CO2 Monitoring and Storage Project, Summary Report 2000-2004" In M. Wilson & M. Monea (Eds.), Proceeings of the 7th International Conference on Greenhouse Gas Control Technologies, Sep. 5-9, 2004, Vancouver, Canada (vol. III). Regina, SK: Petroleum Technology Research Centre.

Wolaver, et al., "Greensites and brownsites: Implications for CO2 sequestration characterization, risk assessment, and monitoring," International Journal of Greenhouse Gas Control, 19, 49-62 (2013).

Yang, et al., "Near-Surface Monitoring of Large-Volume CO2 Onjection at Cranfield: Early Field Test of SECARB Phase III" SPE Journal, 18(3): 486-494, Jun. 2013.

Yang, et al., "Modeling CO2 Release Experiment in the Shallow Subsurface and Sensitivity Analysis" Environmental & Engineering Geoscience, 19(3): 207-220, Aug. 3, 2013.

Zhou, et al., "Noble gas tracing of groundwater/coalbed methane interaction in the San Juan Basin, USA" Geochimica et Cosmochimica Acta, 69, 5413-5428 (2005).

Romanak, et al., "Potential for a Process-based Monitoring Method above Geological Carbon Storage Sites using Dissolved Gases in Freshwater Aquifers" Procedia Earth and Planetary Science, 7, 746-749 (2013).

European Patent Office (ISA), International Search Report and Written Opinion for PCT/US2014/044657 dated Sep. 10, 2014, 12 pp.

Beaubien, et al., "Monitoring of near-surface gas geochemistry at the Weyburn, Canada, CO2-EOR site, 2001-2011" International Journal of Greenhouse Gase Control, Available online Feb. 19, 2013, vol. 16, Supplement 1, pp. S236-S262.

Ecojustice, "Site History, SW30-5-13-W2M Near Weyburn, Saskatchewan, Cameron and Jane Kerr" Clgary, AB: EcoJustice, Sep. 16, 2010.

Emberley, et al., "Monitoring of fluid-rock interaction and CO2 storage through produced fluid sampling at the Weyburn CO2-injection enhanced oil recovery site, Saskatchewan, Canada" Available online Apr. 22, 2005, Applied Geochemistry, 20, 1131-1157.

Fredlund, et al., "Soil Mechanics for Unsaturated Soils"—Power Point Presentation. New York, NY: John Wiley & Sons, Inc. 1993.

Giammanco, et al., "Soil and fumaroles gases of Mount Etna: Geochemistry and relations with volcanic activity" 1998, Jounral of Volcanology and Geothermal Research, 81, 297-310.

Hackett, et al., "Geology and ground-water resources of the Gallatin Valley, Gallatin County, Montana, with a section on Surface-water, and a section on chemical quality of the water USGS Water Supply Paper. 1482" (1960).

Kharaka, et al., "Changes in the chemistry of shallow groundwater related to the 2008 injection of CO2 at the ZERT filed site, Bozeman, Montana" Environ Earth Sci (2010) 60: 273-284.

Klusman, R.W. "Rate measurement and detection of gas microseepage to the atmosphere from an Enhanced Oil Recovery/sequestration project, Rangely, Colorado, USA" Applied Geochemistry, v. 18(2003) pp. 1825-1838.

Klusman, R.W. "Computer modeling of methanotrophic oxidation of hydrocarbons in the unsaturated zone from an Enhanced Oil Recovery/sequestration project, Rangely, Colorado, USA" Applied Geochemistry, V. 21(2006) pp. 1498-1521.

Klusman, R.W. "Detailed compositional analysis of gas seepage at the National Carbon Storage Test Site, Teapot Dome, Wyoming, USA" Applied Geochemistry, v. 21 (2006) pp. 1498-1521.

Klusman, R.W. "Comparison of surface and near-surface geochemical methods for detection of gas microseepage from carbon dioxide sequestration", International Journal of Greenhouse Gas Control 5, (2011) 1369-1392.

Lafleur, Paul Geochemical Soil Gas Survey: A Site Investigation of SW30-5-13-W2M Weyburn Field, Saskatchewan, Monitoring Project No. 2. Saskatoon, SK: Petro-Find Geochem Ltd., Mar. 16, 2011, 64 pp.

Mariotti, et al., "Experimental determination of nitrogen kinetic isotope fractionation: Some principles; illustration for the denitrification and nitrification process" Plant and Soil 62(3): 413-430 (1981).

Marrin, Donn L. "Soil gas sampling and misinterpretation" Ground Water Monitoring Rev., vol. 8, p. 51-54, 1988.

Nicto, et al., "Shallow Subsurface Characterization of Gas Transport in a Playa Wetland", Gas phase dynamics of playa-wetlands: Journal of Environmental Engineering: 124: 1038-1046 (1998).

Ostendorf, et al., "Biodegradation of Hydrocarbon Vapors in the Unsaturated Zone" Water Resource Research, V. 27, No. 4, p. 453-462, 1991.

Pataki, et al., "The application and interpretation of Keeling plots in terrestrial carbon cycle research" Global Biogeochemical Cycles, 17, 22-1-22-14, 2003.

Petroleum Technology Research Centre "IEAGHG Weyburn-Midale CO2 Monitoring and Storage Project"—Response to a Soil Gas Study Performed by Petro-Find Geochem Ltd. Regina, SK: Petroleum Technology Research Centre, http://www.ptrc.ca/siteimages/WMP-Response-to-Petro-Find.pdf. Jan. 19, 2011.

Riding, et al., "The IEA Weyburn CO2 Monitoring and Storage Project: Final report of the European research team" Keyworth, Notthingham, UK: British Geological Survey. 2005.

Romanak, et al., "Process-Based Approach to Soil Gas monitoring at Geologic Carbon Storage Sites" Geophysical Research Letters. 60 (2), 227-239, 2012.

Saskatchewan Ministry of Energy and Resources, 2011, New Saskatchewan Stratigraphic Correlation Chart, internet resource, www.er.gov.sk.ca/stratchart. Revised Jan. 11, 2011.

Schoell, Martin, "Multiple origins of methane in the earth" Chemical Geology, v. 71, p. 1-10. (1998).

Simpson, M.A., "Geology and Groundwater Resources of the Weyburn/Virden Area (62E/F), Saskatchewan" SRC Publication No. R-1210-3-E-93. Saskatoon, SK: Saskatchewan Research Council. (1993). 38 pp.

Smith, et al., "The Occurrence of Ethylene in Anaerobic Soil" Journal of Soil Science, 22, 430-443, 1971.

Spangler, et al., "A shallow subsurface controlled release facility in Bozeman, Montana, USA, for testing near surface CO2 detection techniques and transport models" Environ. Earth Sci. 6. 2010.

Strazisar, et al., "Near-surface monitoring for the ZERT shallow CO2 injection project" International Journal of Greenhouse Gas Control, 3(6): 736-744 (2009).

Striegl, et al., "Carbon dioxide retention and carbon exchange on vadose Quaternary sediments" Geochimica et Cosmochimica Acta, 54(8): 2277-2283 (1990).

Tilley, et al., "Gas maturity and alteration systematics across the Western Canada Sedimentary Basin from four mud gas isotope depth profiles" Organic Geochemistry, vol. 37, Issue 12, Dec. 2006, pp. 1857-1868 (Available online Nov. 21, 2006).

Trium Environmental Inc. "Site assessment Weburn Unit SW30-5-13W2" www.cenovus.com, Nov. 2011.

U.S. Environmental Protection Agency "General technical support document for injection and geologic sequestration of carbon dioxide: subparts RR and UU" Greenhouse Gas Reporting Program, Office of Air & Radiation, Nov. 2010, 98 pp.

U.S. Environmental Protection Agency Mandatory Reporting of Greenhouse Gases: Injection and Geologic Sequestration of Carbon Dioxide; Final Rule, 75 FR 75060. Dec. 1, 2010, 31 pp.

Patent Examination Report No. 1 issued Jun. 24, 2016, for Australian Patent Application No. 201430214, 3 pages.

(56) References Cited

OTHER PUBLICATIONS

U.S. Appl. No. 14/317,836, filed Jun. 27, 2014, Final Office Action mailed Oct. 7, 2016.
U.S. Appl. No. 14/317,836, filed Jun. 27, 2014, Advisory Action mailed Dec. 15, 2016, all pages.

* cited by examiner

PROCESS-BASED APPROACH FOR THE DETECTION OF DEEP GAS INVADING THE SURFACE

CROSS-REFERENCE TO RELATED APPLICATIONS

This application claims priority to U.S. Provisional Application Ser. No. 61/840,224, filed Jun. 27, 2013, the entire contents of which are incorporated herein by reference.

STATEMENT OF FEDERALLY FUNDED RESEARCH

This invention was made with U.S. Government support by the U.S. Department of Energy through the Office of the Governor of Texas (contract DE-FG04-9OAL65847) and the National Energy Technology Laboratory (contract DE FG26-05NT42590) through the Southeast Regional Carbon Sequestration Partnership. The government has certain rights in this invention.

TECHNICAL FIELD OF THE INVENTION

The present invention relates in general to the field of gas detection, and more particularly, to a novel process-based approach for the detection of deep gas invading the surface.

BACKGROUND OF THE INVENTION

Without limiting the scope of the invention, its background is described in connection with detecting gas in the vadose zone.

Measurement, monitoring and verification (MMV) will be required at geologic carbon storage (GCS) sites to document that storage effectively retains $CO_2$ in the subsurface [European Commission, 2009: US EPA, 2010a, b]. MMV can utilize many techniques deployed at a range of depths from the storage reservoir to the atmosphere, however techniques that monitor leakage through the near surface vadose zone are valuable because: (1) the vadose zone is the interface between subsurface storage and release to atmosphere, (2) gases moving through the shallow subsurface are easily and cheaply monitored, and (3) vadose zone monitoring can directly address concerns of landowners living above GCS sites [Shenk et al., 2011].

The most studied and currently widely accepted approach for vadose zone gas monitoring above GCS sites directly measures $CO_2$ concentrations either by extracting vadose zone gas through hollow push probes or by measuring $CO_2$ surface flux with accumulation chambers. Measurements are made in a grid pattern or in areas of concern, such as faults, fractures, or plugged and abandoned wells [Riding and Rochelle, 2009: Strazisar et al., 2009: Furche et al., 2010]. A minimum of 1 year of background concentration measurements is required prior to $CO_2$ injection to document natural seasonal ranges in vadose zone $CO_2$ apart from leakage. If $CO_2$ concentrations statistically exceed the background range during the lifetime of a GCS project, a storage formation release may be indicated. This approach is herein referred to as a "$CO_2$ concentration-based" approach.

A $CO_2$ concentration-based approach has several drawbacks: (1) high variability of $CO_2$ generated in situ could mask a moderate leakage signal; (2) 1 year of background characterization cannot account for $CO_2$ variability from climatic, land use, and ecosystem variations over the lifetime (tens to hundreds of years) of a storage project; (3) background measurements require a long lead time potentially hindering a project's progress; and (4) background $CO_2$ cannot be measured across all potential small diameter leak points within the area of review: therefore, if concerns arise in an area lacking local background measurements, no baseline data exist with which to compare monitored $CO_2$ concentrations.

SUMMARY OF THE INVENTION

In one embodiment, the present invention includes a method of determining the level of deep gas in a near surface formation without the need for background monitoring comprising: measuring $CO_2$, $O_2$, $CH_4$, and $N_2$ levels in percent by volume (or mole fraction) from one or more surface or near surface geological samples; adding the water vapor content to the measured $CO_2$, $O_2$, $CH_4$, and $N_2$ levels in percent by volume (or mole fraction); normalizing the gas mixture to 100% by volume or 1 atmospheric total pressure; and determining the ratios of: $O_2$ versus $CO_2$ to distinguish the general $CO_2$ production and consumption processes whether in-situ or from exogenous deep leakage $CO_2$; $CO_2$ versus $N_2$ to further distinguish whether $CO_2$ is being removed from the near surface formation or $CO_2$ is added from an exogenous deep leakage input; or $CO_2$ versus $N_2/O_2$ to determine the degree of oxygen influx, consumption, or both; wherein the ratios are indicative of natural in situ processes or from the exogenous deep leakage input. In one aspect, an in-situ vadose zone background level of carbon comprises at least one of biologic respiration, methane oxidation, or $CO_2$ dissolution. In another aspect, the presence of a deep gas source of carbon is indicated if the of $N_2$ is less than 76.4% in a water vapor saturated vadose zone environment. In another aspect if the vadose zone environment is dry, the presence of deep gas may be indicated if $N_2$ above 78%. In another aspect, if the level of $O_2$ is determined by gas chromatography without separation of $O_2$ and Argon peaks, the method further comprises subtracting the level of Argon from the level of $O_2$ to determine the actual level of $O_2$. In another aspect, the amount of Argon is calculated equal to $1/63 \times N_2$ concentration. In another aspect, the water vapor is saturated. In another aspect, the amount of water vapor is 2.1 to 2.4%, 2.2 to 2.35%, or 2.3%. In another aspect, the deep $CO_2$ gas versus $CO_2$ from biological respiration is in the near surface formation if the level of $N_2$ is below 76.4%. In another aspect, wherein an $N_2/O_2$ ratio greater than air indicates influx of air and/or $O_2$ consumption. In another aspect, the water vapor content is measured or estimated. In another aspect, the samples are collected in a sealed container and later analyzed in a laboratory.

In one embodiment, the present invention includes a method of determining the level of deep gas in a near surface formation without the need for background monitoring comprising: measuring $CO_2$, $O_2$, $CH_4$, and $N_2$ levels in percent by volume from one or more surface or near surface geological samples; adding the water vapor content to the measured $CO_2$, $O_2$, $CH_4$, and $N_2$ levels in percent by volume and normalizing the gas mixture to 100% by volume or 1 atmospheric total pressure; and determining the ratios of: $O_2$ versus $CO_2$ to distinguish in-situ vadose zone $CO_2$ from exogenous deep leakage $CO_2$; $CO_2$ versus $N_2$ to distinguish whether $CO_2$ is being removed from the near surface formation or $CO_2$ is added from an exogenous deep leakage input; and $CO_2$ versus $N_2/O_2$ to determine the degree of oxygen influx, consumption, or both; wherein the ratios are indicative of natural in situ $CO_2$ or $CO_2$ from the exogenous deep leakage input. In another aspect, an in-situ vadose zone background level of carbon comprises at least one of biologic respiration, methane oxidation, or $CO_2$ dissolution. In another aspect, the presence of a deep gas source of carbon is indicated if the water saturated atmospheric value of $N_2$ is less than 76.4%. In another if the level of $O_2$ is determined by gas chromatography without separation of $O_2$ and Argon peaks, the method further comprises subtracting the level of Argon from the level of $O_2$ to determine the actual level of $O_2$. In another aspect, the amount of Argon is calculated equal to $1/63 \times N_2$ concentration. In another aspect, the water vapor is saturated. In another aspect, the amount of water vapor is 2.1 to 2.4%, 2.2 to 2.35%, or 2.3%. In another aspect, the deep $CO_2$ gas versus $CO_2$ from biological respiration is in the near surface formation if the level of $N_2$ is below 76.4%. In another aspect, wherein an $N_2/O_2$ ratio greater than air indicates influx of air and/or $O_2$ consumption. In another aspect, the water vapor content is measured or estimated. In another aspect, the samples are collected in a sealed container and later analyzed in a laboratory.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

A critical issue for geologic carbon sequestration is the ability to detect $CO_2$ leakage in the vadose zone. The present invention includes a new process-based approach to identify $CO_2$ that has leaked from deep geologic storage reservoirs into the shallow subsurface. Whereas current $CO_2$ concentration-based methods require years of background measurements to quantify variability of natural vadose zone $CO_2$, this new approach examines chemical relationships between vadose zone $N_2$, $O_2$, $CO_2$, and $CH_4$ to promptly distinguish a leakage signal from background $CO_2$. The method uses sequential inspection (1) $O_2$ versus $CO_2$ to distinguish in-situ vadose zone background processes (biologic respiration, methane oxidation, and $CO_2$ dissolution) from exogenous deep leakage input, (2) $CO_2$ versus $N_2$ to further distinguish dissolution of $CO_2$ from exogenous deep leakage input, and (3) $CO_2$ versus $N_2/O_2$ to assess the degree of atmospheric mixing/dilution occurring in the system. The approach was developed at a natural $CO_2$-rich analog site and successfully applied at a $CO_2$-enhanced oil recovery operation where deep gases migrated into the vadose zone. The ability to identify $CO_2$ leakage into the vadose zone without the need for background measurements could decrease uncertainty in leakage detection and expedite implementation of future geologic $CO_2$ storage projects.

To address the problem of separating signal (leaked) from background (in situ generated) $CO_2$ in the vadose zone, the present invention includes, for the first time, a powerful, yet simple geochemical approach to GCS leakage monitoring that does not require background monitoring. Instead, relationships among major fixed gases ($CO_2$, $N_2$, $O_2$, $CH_4$) are used to identify processes that produce and consume vadose zone $CO_2$. It was found herein that the major in situ vadose zone processes in this analysis can distinguish: biologic respiration, $CH_4$ oxidation, dissolution of $CO_2$ and reaction with soil carbonate, and atmospheric mixing.

Vadose zone processes. In the absence of carbon cycling processes, vadose zone gases are dominated by the atmosphere (in dry air, 78% $N_2$, 21% $O_2$, 0.039% $CO_2$, 1.8 ppm $CH_4$), which invades the subsurface via barometric pumping and diffusion. Root and microbial respiration in the vadose zone increases $CO_2$ and decreases $O_2$ relative to the atmosphere [Hanson et al., 2000] and is affected by temperature, soil moisture content, nutrient availability and oxygen supply which vary on diurnal, seasonal, and longer-term climatic timescales [e.g. Luo and Zhou, 2006]. Microbial respiration commonly produces $CO_2$ wherever organic matter, $O_2$, and soil moisture coexist, but when $O_2$ and other electron acceptors such as nitrate and sulfate are depleted, $CH_4$ is eventually produced [Konhauser, 2006]. If $CH_4$ migrates into oxic zones or if environmental change allows $O_2$ influx, $CH_4$ is oxidized to $CO_2$ [Whalen et al., 1990], potentially mimicking a storage formation leak signal. $CH_4$ oxidation is therefore important to identify wherever in situ $CH_4$ is produced or above oil and gas fields where $CH_4$ may seep from deep reservoirs into the vadose zone over geologic time. Soil gas $CO_2$ may be consumed by dissolution into infiltrating water and reaction with carbonate mineral phases [Striegl and Armstrong, 1990], forming a significant $CO_2$ sink. Vadose zone gas concentrations are also affected by invasion of atmosphere into the subsurface [Osterkamp and Wood, 1987], which can be induced by barometric pressure changes but may also result from pressure gradients caused by dissolution of gas into recharging water [Smith and Arah, 1991: Romanak, 1997: Nicot and Bennett, 1998].

Beginning with atmospheric gas concentrations, vadose zone processes alter soil gas geochemistry in predictable ways on the basis of either reaction stoichiometry or decoupling of gas components. Gas concentrations are measured in percent (volume or molar); therefore, any non-reactive addition or subtraction of a gas component will, by definition, dilute or concentrate, respectively, all other gases in similar proportions. The fixed composition of atmosphere, which dominates the vadose zone in the absence of background or leakage processes, provides the starting point from which to assess reactions. $N_2$ is a good measure of dilution and/or enrichment of a gas mixture owing to its abundance in air and non-reactivity which is compromised only in extreme cases of denitrification [Fryar et al., 2000]. Denitrification can be identified by $N_2$ that is depleted in $^{15}N$ relative to atmosphere ($\delta^{15}N=0‰$) [Mariotti et al., 1981], or by $Ar/N_2$ that is significantly less than 0.0119 [Martin et al, 1995].

Figure 1:
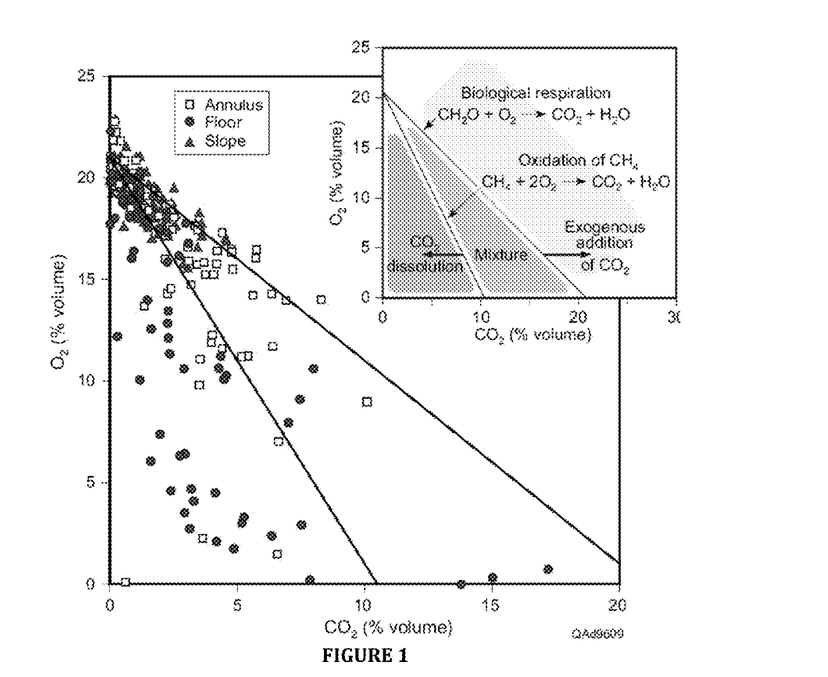
FIG. 1 is a graph that shows soil gas data from a natural $CO_2$-rich playa site shown with general soil gas trends for common background processes of biologic respiration and methane oxidation (lines inside graph). Possible deviations are shown (inset). Gas compositions that plot below both the biological respiration and $CH_4$ oxidation lines indicate $CO_2$ dissolution and reaction with soil carbonate. Data representing a $CO_2$ leak from depth into the vadose zone would plot above these trend lines in the exogenous gas input field.

The process in soils posing the greatest challenge to $CO_2$ concentration based monitoring is $CO_2$ production by oxidation of organic matter during aerobic microbial respiration. This process is represented as:

$$CH_2O + O_2 \rightarrow CO_2 + H_2O \qquad (1)$$

where $O_2$ consumption and $CO_2$ production result in a predictable trend (slope of −1) originating from atmospheric concentrations) on a graph of $CO_2$ versus $O_2$ (FIG. 1). During methane oxidation, $$CH_4 + 2O_2 \rightarrow CO_2 + 2H_2O \qquad (2)$$

$O_2$ consumption and $CO_2$ production produce a trend with a slope of −2 on the same graph. $CO_2$ values higher than expected from corresponding $O_2$ values signal an exogenous $CO_2$ source, indicating a potential leak, and $CO_2$ values lower than expected from corresponding $O_2$ values signal a $CO_2$ sink.

Study sites. The process-based leakage detection approach was developed at a natural $CO_2$-rich ephemeral playa lake in west Texas, USA. Here, known vadose zone processes were coupled with their corresponding soil gas signatures. This information was then successfully applied at an oil field in Mississippi at the site of a plugged and abandoned well to identify anomalous near-surface $CO_2$ and $CH_4$ soil gas signals.

Playa Natural Analog: The playa lakes of west Texas are broad, gently sloping circular basins (~1 to 2 km in diameter) that accumulate and transmit surface runoff through a thick (~60 m) vadose zone. Geomorphic areas associated with playas, which include: slope, annulus, and floor, systematically differ in water flux, organic carbon content, and inorganic soil carbonate, creating spatial variability in the main factors that affect natural vadose zone CO2 production and consumption [Osterkamp and Wood, 1987; Romanak, 1997]. These systematic differences provide an opportunity to link various natural CO2 cycling processes to their vadose zone soil gas signatures. The low-angle playa slope defines the outer edge of the playa basin and transmits storm runoff onto playa floors [Gustayson and Winkler, 1988]. The annulus, a sort of "bathtub ring" defined by a break in slope around the lake's shoreline, transmits water through silty sediments only during high water levels [Hovorka, 1996; Scanlon et al., 1997]. Organic-rich clays and silty clay loams of the flat playa floor pond water before transmitting it along shrink-swell fractures and root tubules through clay deposits [Hovorka, 1996: Scanlon et al., 1997]. Beneath playa floors, dissolved organic carbon is microbially oxidized to produce CO2 which dissolves soil carbonate to create piping and secondary pores as large as 7 mm in diameter (Osterkamp and Wood, 1987).

The specific playa studied herein is located at 35° 25' 2.2" N, 101° 30' 8.4" W, with a diameter of 0.8 km. Soil gas collected during 10 sampling trips between August 1992 and May 1995 was analyzed for CO2, O2, N2, CH4, $\delta$13C of CO2, and 15N of N2 from 23 stations containing 54 semi-permanent soil gas wells at depths ranging from 0.6 to 13.7 m. Stations were installed along radial transects extending through slope, annulus and floor areas to identify variations in soil gas concentrations under varying environmental conditions.

Industrial Oil Field Site. Methods applied at the playa study were applied at an area named the P-site at the Cranfield oil field 18 km east of Natchez Miss., USA (31° 34'

11.8" N, 91° 9' 27.4" W) where oil production from the Tuscaloosa Formation (3050 m began in 1944 [Hines, 1950]. Depletion of the field by 1966 was followed by plugging and abandonment of approximately 100 wells in the 31 km² oil field. $CO_2$-enhanced oil recovery (EOR) began in 2008 by Denbury Resources Inc.

Vadose zone monitoring at the P-site began before local $CO_2$ injection. At the site, 13 multi-depth gas sampling stations with a total of 39 gas wells as deep as 3 m were installed in various locations around an 1124 m² gravel pad. One transect extends from an open pit used during 1950s oil production, across the gravel pad near a plugged and abandoned well, and out onto a grassy clearing defined as a background location. Data from portions of this major transect collected over a one-year period.

At both study sites, semi-permanent gas wells were used to sample gas from different depths within the vadose zone (see Well Station Construction, below). This installation type provides: (1) depth profiles of subsurface gas distribution, (2) potential for repeat sampling with exact spatial matching, and (3) sediment samples for assessment of parameters important to reactive transport modeling, soil contamination, or soil/water interactions. Boreholes were as deep as 14 m and well placement was targeted to areas of concern identified through reconnaissance sampling using a standard push probe.

Well Station Construction. Semi-permanent soil gas sampling stations were comprised of multiple sampling tubes (0.64-cm copper tubing at the playa and 0.32-cm stainless steel tubing at Cranfield) installed at depths of interest within each 5-cm diameter borehole. [Note: Wells can generally be installed in any size borehole that will accommodate the number of wells desired however larger diameter holes require more material for back-filling. Generally 5 cm diameter boreholes are desirable and will accommodate up to four wells]. Before drilling, all underground infrastructures were identified to avoid hitting gas or electrical lines. At the down-hole end of the Cranfield gas sampling wells, 152 mm stainless steel mesh screens (Geoprobe 15-cm vapor implants) were connected with Swagelok gas-tight fittings. Screens were set in 20-30 cm of quartz sand. The borehole was then backfilled with wetted bentonite clay chips to isolate the sampling interval until the next sampling level was reached. The process was repeated until all gas sampling wells were set in sand pack and their sampling intervals isolated with bentonite. Each gas sampling well was carefully labeled with its depth and topped with either a rubber tip (playa) or a noflow Swagelok quick connect stem (SS-QM2-D-200) that stops air from entering the tube until it is joined to the sampling hose with a quick connect body (SS-QM2-B-200) (Cranfield). All gas well tubing was cut at similar heights above ground surface (~0.3 to 0.5 meters). When the borehole was filled to within 0.5 m of ground surface, a PVC protector pipe was installed over the sampling tubes, inserted into the remaining space within the borehole and secured by adding wetted bentonite around the annulus to hold it in place. The pipe was capped and labeled and protected the gas sampling wells from environmental damage.

Field GC Analysis. A Masterflex E/S portable peristaltic pump was used to draw soil-gas from wells at a flow rate of approximately 50 to 100 cc/min and deliver the sample to the gas chromatograph (GC) through tygon tubing directly plumbed to the inlet of the GC sample loop. During sampling, either an in-line pressure gauge for monitoring well pressure or a flow meter for monitoring flow rate were used to verify that no vacuum pressure developed risking dilution with ambient air or cross contamination from other sampling depths. Prior to GC analysis, the sample line to the well was purged for a sufficient time to void 2-3 well/sample line volumes. Sampling at each well continued until three runs with stable concentrations within ±10% relative difference) for each analyte were obtained. The GC was calibrated using air and certified low and high standard gas mixtures (Scot brand) spanning expected nominal concentration ranges before, during, and after each day's sampling. The precision for both detectors is ±2%.

On-site analysis of major gas compounds ($CO_2$, $O_2$, $N_2$, and $CH_4$) was accomplished at both sites using a portable gas chromatograph (SRI 8610) fixed with a CTR2 binary column (Porapak Q and molecular sieve), thermal conductivity (TCD) and flame ionization (FID) detectors, hydrogen carrier gas at various flow rates (35-46 mls/min), and isothermal temperatures of 30-45° C. A methanizer on the FID brought detection limits for $CO_2$ down to atmospheric concentrations. This chromatographic method does not separate argon (Ar) from $O_2$, therefore, Ar was estimated at 1/83 of N2 and subtracted from the $O_2$ measurement which is acceptable when denitrification is insignificant N2 [Smith and Arah, 1991]. 2.2% water vapor representing saturated water vapor pressure was added to all measurements. All sample measurements were normalized to 100% for comparison purposes due to slight differences in the inlet pressures at the GC sample loop from variations in pumping rates.

Laboratory Analysis. Gas samples for δ13C and δ15N were collected in stainless steel gas cylinders with Swagelok fittings at the playa site and in pre-evacuated Cali 5-bond gas bags at Cranfield. Carbon isotopes for the playa study were analyzed by mass spectrometer at Coastal Isotope Laboratories in Austin Tex. (δ13C relative to PDB standard with a precision of ±0.2%). δ15N was measured by mass spectrometer at the Department of Environmental Sciences at the University of Virginia with atmospheric nitrogen as the standard and precision±0.15%). δ13C of CO2 and CH4 and δD of CH4 at Cranfield were collected in preevacuated Cali 5-bond gas bags and analyzed at Isotech Laboratories (Champaign, Ill.) using a GC-CIRMS system. This method employs a GC combustion unit interfaced with a mass spectrometer (Delta V Plus or Delta Plus Advantage). Samples are injected into the GC split/splitless injector and are separated by the GC column. Each individual hydrocarbon (CH4) component is combusted and the resultant CO2 is introduced directly into the mass spectrometer. Hydrogen isotopic values for methane are completed using the same system, but the gas is channeled through a high-temperature pyrolysis furnace instead of through the combustion furnace. The pyrolysis furnace converts methane into H2 and carbon, and the H2 gas is introduced directly into the mass spectrometer. Nitrogen isotopic data for elemental nitrogen (N2) is generated using the same system. For measurement of isotopes of CO2, the gas does not pass through a combustion furnace but is channeled directly from the GC outlet to the collection trap. Stated precision for δ13C is ±0.3% and for δD±2.0%.

Major gas compounds ($CO_2$, $O_2$, $N_2$, and $CH_4$) were analyzed on-site at both study areas using a portable gas chromatograph. Samples were also collected for laboratory isotope analyses including $\delta^{13}C$ of $CO_2$ and $CH_4$, δD of $CH_4$, and $^{15}N$ of $N_2$. Playa samples were collected in stainless steel gas cylinders with Swagelok fittings and analyzed either by mass spectrometer at Coastal Laboratories, Austin, Tex. ($\delta^{13}C$ of $CO_2$) or at the University of Virginia ($\delta^{15}N$ of $N_2$). Isotopes of Cranfield gases ($\delta^{13}C$ of $CO_2$ and $CH_4$, and δD of $CH_4$) were collected in Cali-5-bond bags and analyzed at Isotech Laboratories, Champaign, Ill. by mass spectrometer.

Natural Analog Playa Site. In the playa, maximum concentrations of $CO_2$ (slope: 5.0%, annulus: 10.5%, floor: 17.2%) and $CH_4$ (slope: 0%, annulus: 2.2%, floor: 0.9%), coupled with minimum $O_2$ (slope: 15.6%, annulus: 0.1%, and floor 0.0%) indicate that microbial $CO_2$ and $CH_4$ production is relatively low in the slope, where organic carbon content and water flux is low, and high in the floor, where organic carbon content and water flux is high. The annulus is a transitional zone, behaving like the slope when dry and the floor when high water levels allow water infiltration through annulus sediments.

Figure 5:
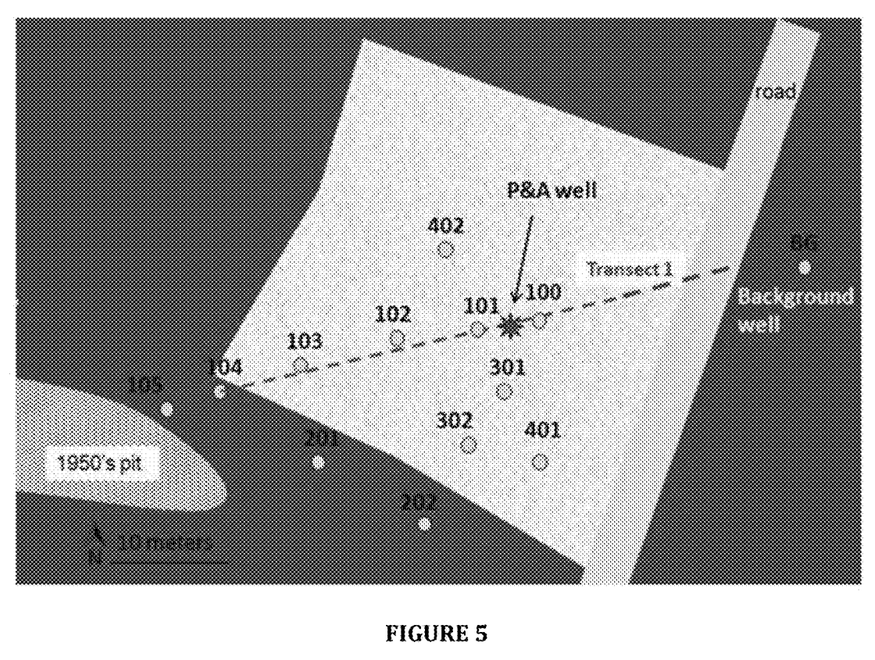
FIG. 5 is a map showing gas sampling locations at the p-site, Cranfield oilfield. Data are reported for stations BG, 100, 101, 103. Additional drilling sites are labeled 102, 104, 105, 201, 202, 301, 302, 401 and 402. The main transect is indicated by the hashed line.

FIG. 5 is a map showing gas sampling locations at the p-site, Cranfield oilfield. Data are reported for stations BG, 100, 101, 103. Additional drilling sites are labeled 102, 104, 105, 201, 202, 301, 302, 401 and 402. The main transect is indicated by the hashed line.

Figure 2:
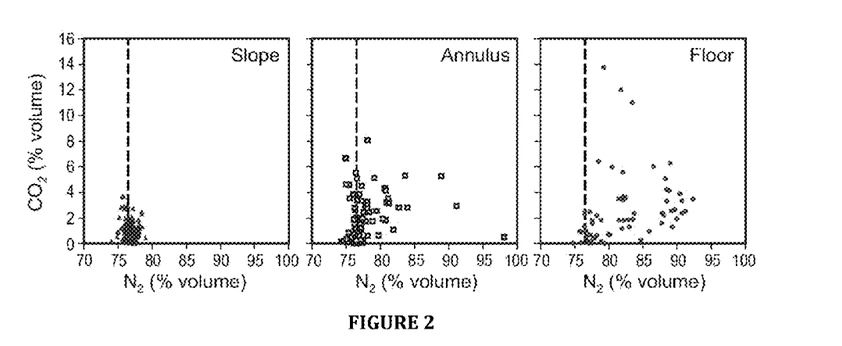
FIG. 2 shows three graphs that show a comparison of trends in $CO_2$ versus $N_2$ for various natural playa zones (slope, annulus, floor). Dashed line indicates atmospheric $N_2$ concentration in water vapor saturated soils (76.4%). Enrichment of $N_2$ concentrations above atmospheric values (samples to the right of the dashed line) indicates that the background process of $CO_2$ dissolution into recharging groundwater has occurred. If samples lie significantly to the left of the dashed line, exogenous gas input from deep reservoir leakage may be indicated.
Figure 6:
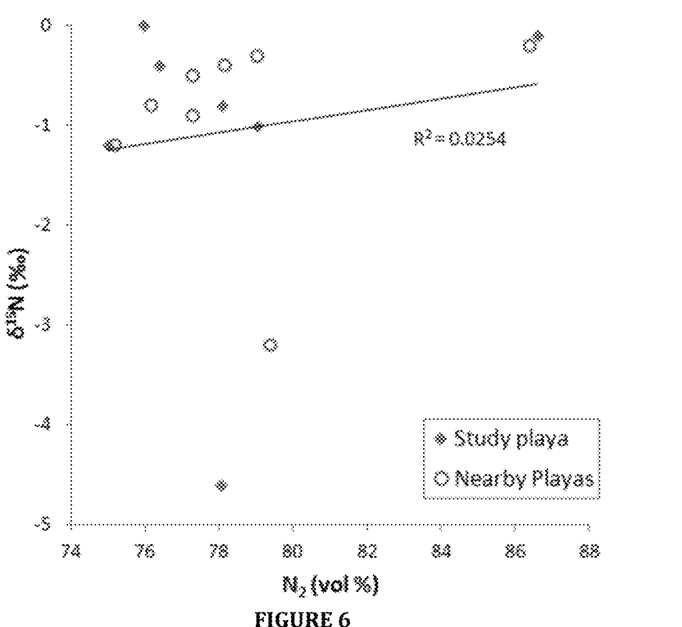
FIG. 6 is a graph of $\delta^{15}N$ versus $N_2$ concentrations for the study playa and for two other nearby playas in west Texas. Location information on additional playas as well as a discussion about nitrogen in playas can be found in Fryar et al. (2000). The data indicate little co-variation between the two parameters suggesting that although denitrification does occur, it is not significantly affecting nitrogen concentrations beneath playas.

Gas compositions from the slope and annulus, and a few from the floor, cluster between trends for microbial respiration and $CH_4$ oxidation on a graph of $CO_2$ versus $O_2$ with some analytical scatter (FIG. 1). Many samples from the playa floor lie below both trend lines indicating a loss of $CO_2$ from the gas phase. Samples that indicate this loss of $CO_2$ (most gas compositions from the floor and some from the annulus) generally also exhibit $N_2$ values enriched above atmospheric values (FIG. 2). Nitrogen isotope ratios of gas sampled from three area playas show insignificant denitrification, indicated by a lack of covariation between $N_2$ and $^{15}N$ ($R^2$=0.0254) for 15 samples (FIG. 6). Comparison of $N_2$ and $CO_2$ concentrations from each playa zone (FIG. 2) shows the following relationships: (1) $N_2$ values in the slope (74.0-79.0%) resemble those of the atmosphere, (2) $N_2$ values in the floor (74.8-92.4%) are predominantly enriched relative to the atmosphere, and (3) $N_2$ signatures in the annulus (74.3-98.1%) are mixed, depending on whether the annulus was wet and undergoing infiltration or dry.

$N_2$ concentrations enriched relative to the atmosphere suggest the dissolution of $CO_2$ into recharging groundwater enhanced by concurrent dissolution of soil carbonate. The loss of $CO_2$ from the gas phase enriches the percent concentration of $N_2$ above atmospheric values. $N_2$ enrichment is augmented by advection of the atmosphere into soil pores driven by the pressure differential created from loss of $CO_2$ gas [Smith and Arah, 1991: Nicot and Bennett, 1998].

Figure 3:
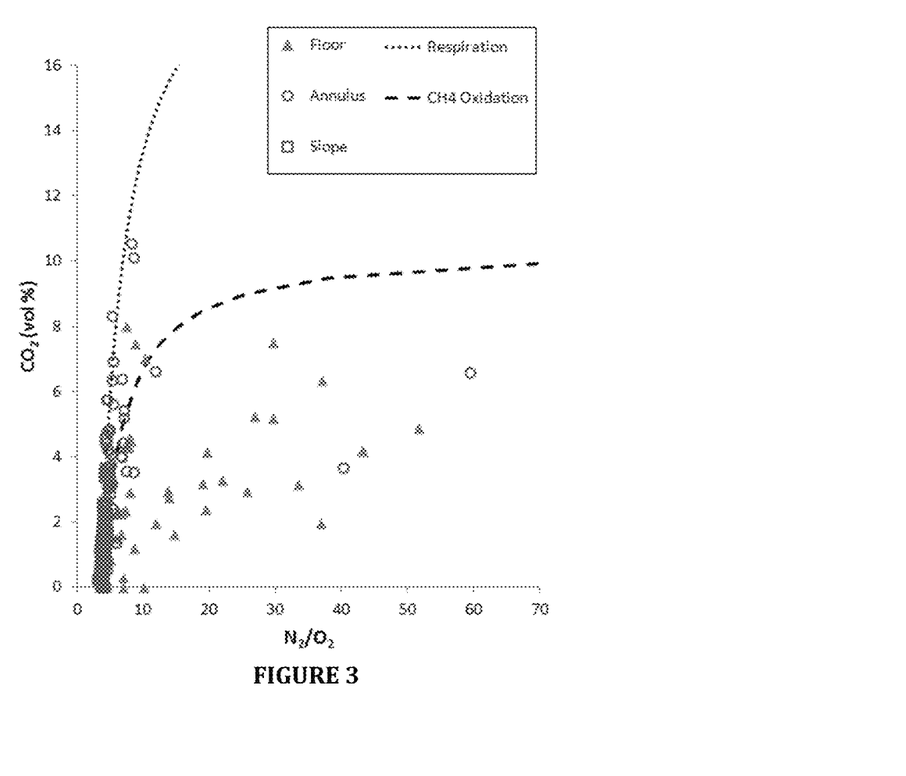
FIG. 3 is a graph that shows the gas composition relationships of $CO_2$ versus $N_2/O_2$ for the playa study site. Trends for $O_2$ consumption during biologic respiration and $CH_4$ oxidation are shown. These relationships distinguish the amount of oxygen input and utilization. In a natural system with no exogenous input from depth, gases that undergo $CO_2$ dissolution and mixing with air will migrate to lower $CO_2$ concentrations and higher $N_2/O_2$ ratios.

Oxygen consumption during $CH_4$ oxidation, and to a lesser degree from microbial respiration, is identified by $N_2/O_2$ above the atmospheric ratio of 3.8 (FIG. 3), in the absence of significant denitrification. Whereas both atmospheric mixing and $CO_2$ dissolution retain a 3.8 ratio, $O_2$ consumption increases this ratio. At the playa, $O_2$ consumption from microbial respiration increases $N_2/O_2$ to as high as 10, whereas $CH_4$ oxidation coupled with air influx increases this ratio to as high as 60 (FIG. 3). $N_2/O_2$ is therefore an indicator of the magnitude of oxygen influx and consumption, which can be an indicator of $CH_4$ oxidation and discriminates microbial respiration and carbonate dissolution from $CH_4$ oxidation which is an especially important distinction in hydrocarbon fields where oxidized $CH_4$ seepage could be mistaken for a $CO_2$ leak.

Figure 7:
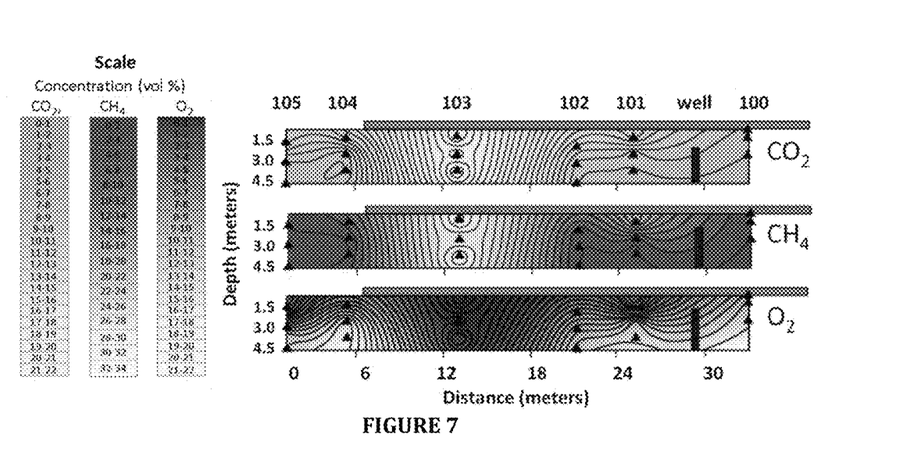
FIG. 7 shows a cross section of $CO_2$ (≤21.4%), $CH_4$ (≤33.3%), and $O_2$ (0-21%) gas concentrations along the main gas sampling transect at the Cranfield oil field near the soil gas anomaly (centered at 103, see FIG. 5 for numbered locations). Light colors indicate high concentrations; dark colors indicate low concentrations (scale at left). The cross section is presented to show the general distribution of gases in the subsurface. High concentrations of $CO_2$ and $CH_4$ correspond with low $O_2$. Gas diffusion gradients favor lateral migration near the anomaly and vertical migration away from the anomaly. $O_2$ appears to invade the subsurface at some distance from the anomaly epicenter migrating laterally at depth.
Figure 8:
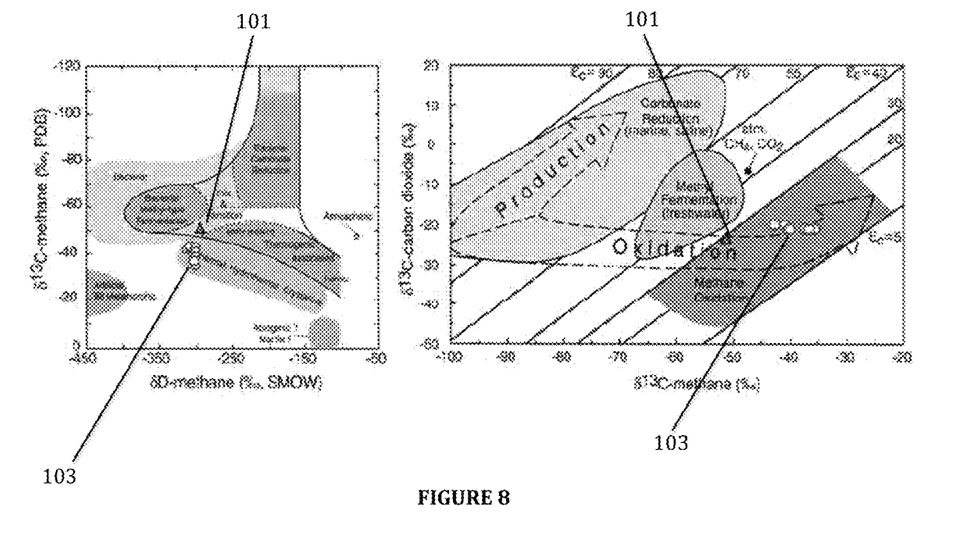
FIG. 8 shows an assessment of isotopic data from the Cranfield oil field using the system of Whiticar (1999). Blue triangle=station 101; red circles=anomaly well 103. The data indicate that $CH_4$ from well 103 originates from a deep exogenous source (i.e. the oil and gas reservoir) and $CO_2$ originates from methane oxidation. As expected, these relationships are less apparent at station 101, farther from the anomaly. The exogenous source of gas and the process of methane oxidation are successfully identified using the process-based method of analysis.

Industrial Site Cranfield Results. The base concept that background processes can be distinguished from a leakage signal using soil gas geochemical relationships was tested at the Cranfield oil field. Here, a persistent $CO_2$ (44.7%) and $CH_4$ (33.5%) anomaly is centered along a 55 m soil gas sampling transect near a plugged and abandoned well (FIGS. 5 and 7). $CO_2$ and $CH_4$ concentrations decrease and $O_2$ generally increases away from the anomaly along the 43 m that separate the anomaly and background locations. Gas sampled from the anomaly shows isotopic relationships for $CH_4$ ($δ^{13}C$ −36.7 to −42.4‰: δD −305.0 to −310.2‰) and $CO_2$ ($δ^{13}C$, −18.6 to −19.8‰) that are consistent with a deep thermogenic $CH_4$ source and $CO_2$ derived from $CH_4$ oxidation (Whiticar, 1999: FIG. 8. These data confirm that the vadose-zone anomaly is exogenous gas originating from depth and provides an unambiguous setting in which to test the potential of the process-based method to perform in less obvious leakage detection scenarios.

Figure 4:
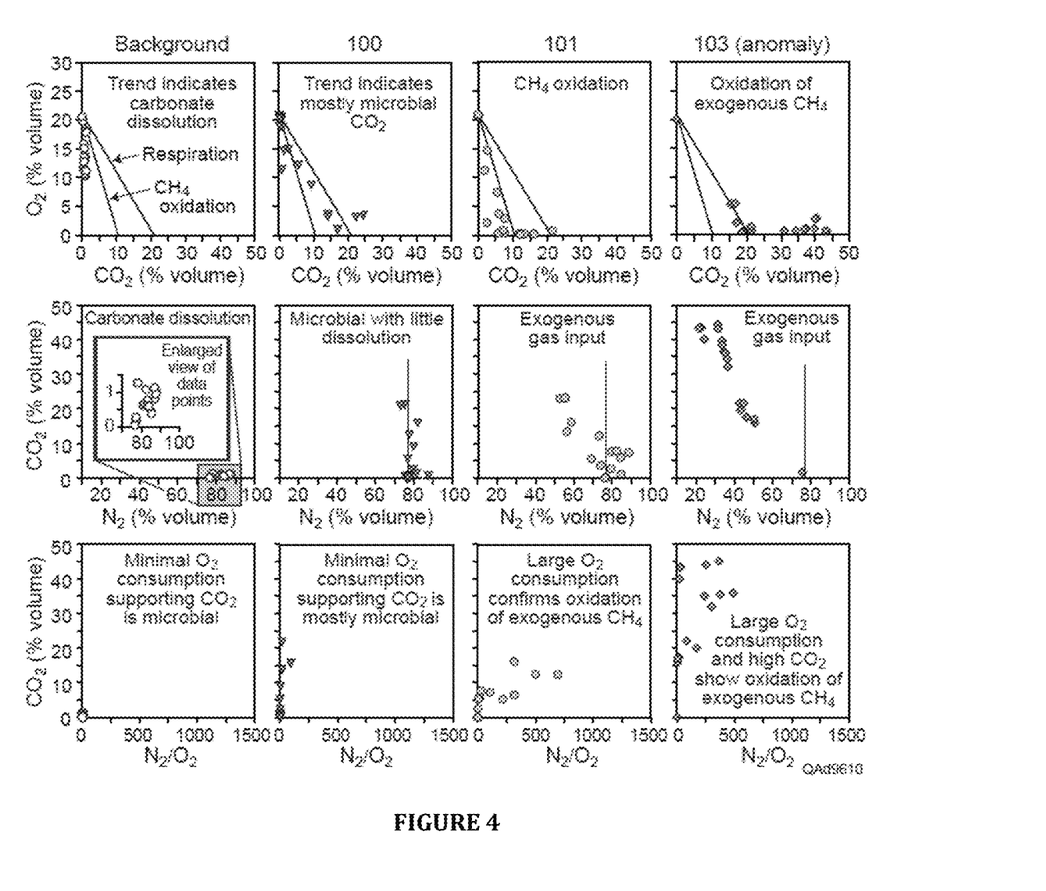
FIG. 4 shows twelve graphs that summarize the vadose zone gas data from selected wells along a gas sampling transect extending from a background location to a vadose zone gas anomaly at the P-site at the Cranfield oil field. Systematic trends (previously discussed and identified in FIGS. 1-3, at sites 100, 101 and 103 of FIG. 5) indicate that gas concentration relationships can distinguish natural background processes from exogenous gas input.

To further confirm the methodology, key gas concentration relationships ($CO_2$ vs. $O_2$, $CO_2$ vs. $N_2$, and $CO_2$ vs. $N_2/O_2$) developed at the playa site were systematically observed from the background well toward the anomaly (FIG. 4). In the background well, gas compositions fall well below the respiration and $CH_4$ oxidation trends on a graph of $O_2$ versus $CO_2$ indicating the background process of $CO_2$ dissolution and reaction with soil carbonate. In situ processes are further supported by $N_2$ concentrations enriched with respect to the atmosphere. $O_2/N_2$ is near atmospheric ratios indicating no $CH_4$ oxidation.

As the anomaly is approached along the transect, soil gas relationships between $CO_2$ and $O_2$ shift systematically toward the $CH_4$ oxidation trend line, then to low $O_2$ concentrations along that line, and finally to the right of the biologic respiration trend in the leakage field (FIG. 4). This progressive transformation represents an increasing magnitude of $CH_4$ oxidation as the anomaly is approached which eventually manifests as an exogenous source plotting in the leakage field. $N_2$ versus $CO_2$ also shifts as the anomaly is approached from a background $CO_2$ dissolution signal to one that signifies input of exogenous gas ($N_2$ concentrations<atmospheric values). $N_2/O_2$ ratios much greater than air correctly indicate persistent $CH_4$ oxidation and influx of air.

The present invention provides for the first time a new approach to separate leakage signal in the vadose zone above GCS sites from relatively complex natural $CO_2$ cycling processes without the need for background data. The approach uses three major soil gas concentration relationships ($CO_2$ vs. $O_2$, $CO_2$ vs. $N_2$, and $CO_2$ vs. $N_2/O_2$) to identify the vadose zone processes of biologic respiration, $CH_4$ oxidation, soil carbonate and $CO_2$ dissolution, atmospheric mixing, and input of exogenous gas ($CO_2$ and/or $CH_4$). Natural background processes were identified at a $CO_2$-rich playa lake in west Texas and using these techniques that were then successfully applied at an industrial oil field site near Cranfield, Miss., where exogenous gas input from depth reached the surface. At the Cranfield site, gas concentration relationships indicating natural processes shifted systematically to those indicating an exogenous gas source as a surface gas anomaly was approached. Success of the process-based approach to identify deep gas in the vadose zone at an industrial site represents a significant advance in our ability to detect $CO_2$ leakage from depth into the vadose zone at $CO_2$ storage sites.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

European Commission (2009), Directive 2009/31/EC of the European Parliament and of the Council of 23 Apr. 2009 on the geological storage of carbon dioxide: Official Journal of the European Union L 140/114 EN.

Fryar, A. E., S. A. Macko, W. F. Mullican, K. D. Romanak, and P. C. Bennett (2000), Nitrate reduction during ground-water recharge, Southern High Plains, Tex.: Journal of Contaminant Hydrology 40, 335-363.

Furche, M., S. Schlomer, E. Faber, and I. Dumke (2010), One year continuous vadose zone gas monitoring above an EGR test site Geophysical Research Abstracts Vol. 12, EGU2010-3095-1, 2010 7th EGU General Assembly 2010.

Gustayson, T. C., and D. A. Winkler (1988), Depositional facies of the Miocene-Pliocene Ogallala Formation, northwestern Texas and eastern New Mexico: Geology, 16(3): 203-206.

Hanson, P. J., N. T. Edwards, C. T. Garten, and J. A. Andrews (2000), Separating root and soil microbial contributions to soil respiration: A review of methods and observations: Biogeochemistry, 48: 115-146.

Hines, L., (1950), The Cranfield: World Oil, February: 131-146.

Hovorka, S. D., (1995), Quaternary evolution of playa lakes on the Southern High Plains—a case study from the Amarillo area, Texas: The University of Texas at Austin, Bureau of Economic Geology Report of Investigations No. 236, 52 p.

Konhauser, K. (2006), Introduction to geomicrobiology: Maldon, Oxford, Carlton: Blackwell Publishing, 425 p.

Luo, Y., and X. Zhou (2006), Soil respiration and the environment: Elsevier Academic Press Amsterdam, 334 p.

Mariotti, A., J. Germon, P. Hubert, P. Kaiser, R. Letolle, A. Tardieux, and P. Tardieux (1981), Experimental determination of nitrogen kinetic isotope fractionation: Some principles; illustration for the denitrification and nitrification processes: Plant and Soil 62(3): 413-430.

Martin, G. E., D. D. Snow, K. Euisik, and R. F. Spalding (1995), Simultaneous determination of Argon and Nitrogen: Ground Water 33(5): 781-785.

Nicot, J. P., and P. C. Bennett (1998), Gas phase dynamics of playa-wetlands: Journal of Environmental Engineering: 124: 1038-1046.

Osterkamp, W. R. and W. W. Wood (1987), Playa-lake basins on the Southern High Plains of Texas and New Mexico: Part 1: Hydrologic, geomorphic, and geologic evidence for their development: GSA Bulletin, 99: 215-223.

Riding, J. B., and C. A. Rochelle, (2009), Subsurface characterisation and geological monitoring of the CO2 injection operation at Weyburn, Saskatchewan, Canada in D. J. Evans and R. A. Chadwick, eds., Underground gas storage: worldwide experiences and future development in the UK and Europe: London, Geological Society, Special Publication 313: 227-256.

Romanak, K. D. (1997), Vadose-zone geochemistry of playa wetlands, High Plains, Tex.: The University of Texas at Austin, Ph.D. dissertation, 273 p.

Sherk, G. W., Romanak, K. D., Dale, J., Gilfillan, S. M. V., Haszeldine, R. S., Ringler, E. S., Wolayer, B. D., and Yang, C., (2011), The Kerr investigation: findings of the investigation into the impact of $CO_2$ on the Kerr property: IPAC Research Inc., final report prepared for property owners Cameron and Jean Kerr, 181 p.

Scanlon, B. R., R. S. Goldsmith, and W. F. Mullican III (1997), Spatial variability in vadose flow beneath playa and adjacent interplaya settings and implications for contaminant transport, Southern High Plains, Tex.: The University of Texas at Austin, Bureau of Economic Geology Report of Investigations No. 243, 56 p.

Smith, K. A., and J. R. M. Arah, (1991), Gas chromatographic analysis of the soil atmosphere, in K. Smith, ed., Soil analysis: Marcel Dekker, New York, 505-546.

Strazisar, N. R., A. W. Wells, J. R. Diehl, R. W. Hammack, and G. A. Veloski, (2009), Near-surface monitoring for the ZERT shallow CO2 injection project: International Journal of Greenhouse Gas Control, 3(6): 736-744.

Striegl, R. G. and D. E. Armstrong, (1990), Carbon dioxide retention and carbon exchange on vadose Quaternary sediments: Geochimica et Cosmochimica Acta, 54(8): 2277-2283.

USEPA (2010a), General technical support document for injection and geologic sequestration of carbon dioxide: subparts RR and UU.

USEPA (2010b), Mandatory reporting of greenhouse gases: injection and geologic sequestration of carbon dioxide; final rule, 75 FR 75060.

Whalen, S. C., W. S. Reeburgh, and K. A. Sandbeck, (1990), Rapid methane oxidation in a landfill cover soil Applied Environmental Microbiology, 56(11): 3405-3411.

Whiticar, (1999), Carbon and hydrogen isotope systematics of bacterial formation and oxidation of methane: Chemical Geology, 161: 291-314.

What is claimed is:

1. A method of determining a level of deep gas in a near surface formation without a need for background monitoring comprising:
    measuring $CO_2$, $O_2$, $CH_4$, and $N_2$ levels in percent by volume from one or more surface or near surface geological samples;
    transforming the measured $CO_2$, $O_2$, $CH_4$, and $N_2$ levels by adding water vapor content to the measured $CO_2$, $O_2$, $CH_4$, and $N_2$ levels in percent by volume;
    normalizing the $CO_2$, $O_2$, $CH_4$, and $N_2$ levels to 100% by volume or 1 atmosphere total pressure to generate normalized $CO_2$, $O_2$, $CH_4$, and $N_2$ levels;
    determining the ratios of:
        the normalized $O_2$ level versus the normalized $CO_2$ level to distinguish in-situ vadose zone $CO_2$ from exogenous deep leakage $CO_2$; and
        the normalized $CO_2$ level versus the normalized $N_2$ level to distinguish whether $CO_2$ is being removed from the near surface formation or $CO_2$ is added from an exogenous deep leakage input; or the normalized $CO_2$ level versus the normalized $N_2$ level divided by the normalized $O_2$ level to determine a degree of oxygen influx, consumption, or both oxygen influx and consumption; and
    evaluating the ratios to determine whether $CO_2$ present in the surface or near surface geological samples is from natural in-situ $CO_2$ or $CO_2$ from exogenous deep leakage without a need for background monitoring, wherein evaluating includes identifying $CO_2$ from exogenous deep leakage if the normalized $N_2$ level is less than 78% under dry conditions, wherein evaluating includes identifying $CO_2$ from natural in-situ $CO_2$ if the normalized $N_2$ level is about 78% under dry conditions, or wherein evaluating includes identifying air influx into the near surface formation if the normalized $N_2$ level divided by the normalized $O_2$ level is greater than a ratio of $O_2$ to $N_2$ in air.

2. The method of claim 1, wherein an in-situ vadose zone background level of carbon comprises at least one of biologic respiration, methane oxidation, or $CO_2$ dissolution.

3. The method of claim 1, wherein a presence of a deep gas source of carbon is indicated if the normalized $N_2$ level under water saturated conditions is less than 76.4%.

4. The method of claim 1, wherein if the normalized $O_2$ level is determined by gas chromatography without separation of $O_2$ and Argon peaks, the method further comprises subtracting an amount of Argon from the normalized $O_2$ level to determine an actual $O_2$ level.

5. The method of claim 4, wherein the amount of Argon is calculated equal to 1/63× the normalized $N_2$ level.

6. The method of claim 1, wherein the water vapor content corresponds to water saturated conditions.

7. The method of claim 1, wherein an amount of the water vapor content is 2.1 to 2.4%.

8. The method of claim 1, further comprising installing gas probes into the near surface formation for measuring the $CO_2$, $O_2$, $CH_4$, and $N_2$ levels.

9. The method of claim 1, wherein the water vapor content is measured or estimated.

10. The method of claim 1, wherein the one or more surface or near surface geological samples are collected in a sealed container and later analyzed in a laboratory.

11. A method of determining a level of deep gas in a near surface formation without a need for background monitoring comprising:
    measuring $CO_2$, $O_2$, $CH_4$, and $N_2$ levels in percent by volume from one or more surface or near surface geological samples;
    transforming the measured $CO_2$, $O_2$, $CH_4$, and $N_2$ levels by adding water vapor content to the measured $CO_2$, $O_2$, $CH_4$, and $N_2$ levels in percent by volume;
    normalizing the $CO_2$, $O_2$, $CH_4$ and $N_2$ levels to 100% by volume or 1 atmosphere total pressure to generate normalized $CO_2$, $O_2$, $CH_4$ and $N_2$ levels;
    determining the ratios of:
        the normalized $O_2$ level versus the normalized $CO_2$ level to distinguish in-situ vadose zone $CO_2$ from exogenous deep leakage $CO_2$;
        the normalized $CO_2$ level versus the normalized $N_2$ level to distinguish whether $CO_2$ is being removed from the near surface formation or $CO_2$ is added from an exogenous deep leakage input; and
        the normalized $CO_2$ level versus the normalized $N_2$ level divided by the normalized $O_2$ level to determine a degree of oxygen influx, consumption, or both oxygen influx and consumption; and
    evaluating the ratios to determine whether $CO_2$ present in the surface or near surface geological samples is from natural in-situ $CO_2$ or $CO_2$ from exogenous deep leakage without a need for background monitoring, wherein evaluating includes identifying $CO_2$ from exogenous deep leakage if the normalized $N_2$ level is less than 78% under dry conditions, wherein evaluating includes identifying $CO_2$ from natural in-situ $CO_2$ if the normalized $N_2$ level is about 78% under dry conditions and wherein evaluating includes identifying air influx into the near surface formation if the normalized $N_2$ level divided by the normalized $O_2$ level is greater than a ratio of $O_2$ to $N_2$ in air.

12. The method of claim 11, wherein an in-situ vadose zone background level of carbon comprises at least one of biologic respiration, methane oxidation, or $CO_2$ dissolution.

13. The method of claim 11, wherein the presence of a deep gas source of carbon is indicated if the normalized $N_2$ level under water saturated conditions is less than 76.4%.

14. The method of claim 11, wherein if the normalized $O_2$ level is determined by gas chromatography without separation of $O_2$ and Argon peaks, the method further comprises subtracting an amount of Argon from the normalized $O_2$ level to determine an actual $O_2$ level.

15. The method of claim 14, wherein the amount of Argon is calculated equal to 1/63× the normalized $N_2$ level.

16. The method of claim 11, wherein the water vapor content corresponds to water saturated conditions.

17. The method of claim 11, wherein an amount of the water vapor content is 2.1 to 2.4%.

18. The method of claim 11, further comprising installing probes into the near surface formation for measuring the $CO_2$, $O_2$, $CH_4$, and $N_2$ levels.

19. The method of claim 11, wherein the water vapor content is measured or estimated.

20. The method of claim 11, wherein the one or more surface or near surface geological samples are collected in a sealed container and later analyzed in a laboratory.

* * * * *